United States Patent
Liu

(10) Patent No.: US 11,554,163 B2
(45) Date of Patent: Jan. 17, 2023

(54) USE OF PROUROKINASE AND ITS VARIANTS AGAINST COAGULOPATHY CAUSED BY VIRUSES

(71) Applicant: Jianning Liu, Suzhou (CN)

(72) Inventor: Jianning Liu, Suzhou (CN)

( * ) Notice: Subject to any disclaimer, the term of this patent is extended or adjusted under 35 U.S.C. 154(b) by 174 days.

(21) Appl. No.: 17/105,867

(22) Filed: Nov. 27, 2020

(65) Prior Publication Data

US 2022/0023397 A1 Jan. 27, 2022

(30) Foreign Application Priority Data

Jul. 26, 2020 (CN) .......................... 202010726926.4

(51) Int. Cl.
*A61K 38/48* (2006.01)
*A61K 9/00* (2006.01)

(52) U.S. Cl.
CPC .......... *A61K 38/482* (2013.01); *A61K 9/0019* (2013.01); *C12Y 304/21073* (2013.01)

(58) Field of Classification Search
CPC .... A61K 38/482; A61K 9/0019; A61K 38/49; C12Y 304/21073
See application file for complete search history.

(56) References Cited

FOREIGN PATENT DOCUMENTS

CN 1277262 A 12/2000

OTHER PUBLICATIONS

Dimakakos E, Grapsa D, Vathiotis I, Papaspiliou A, Panagiotarakou M, Manolis E, Syrigos K. H1N1-Induced Venous Thromboembolic Events? Results of a Single-Institution Case Series. Open Forum Infect Dis. Dec. 20, 2016;3(4):ofw214. doi: 10.1093/ofid/ofw214. PMID: 28018924; PMCID: PMC5170496.*
Moia M, Mannucci PM, Pini M, Prandoni P, Gurewich V. A pilot study of pro-urokinase in the treatment of deep vein thrombosis. Thromb Haemost. Sep. 1994;72(3):430-3. PMID: 7531876.*
Gursky Y, Bibilashvili R, Minashkin M, Krasnov A, Deikin A, Ermolkevich T, Popov A, Verbovaya L, Rutkevich N, Shevelev A, Georgieva S, Razin SV, Goldman I, Sadchikova E. Expression of full-length human pro-urokinase in mammary glands of transgenic mice. Transgenic Res. Oct. 2009;18(5):747-56. doi: 10.1007/s11248-00.*
"Extremely High Incidence of Lower Extremity Deep Venous Thrombosis in 48 Patients With Severe COVID-19 in Wuhan" Bin Ren, et al., Circulation. 2020;142:181-183. DOI: 10.1161/CIRCULATIONAHA.120.047407.
"ISTH interim guidance on recognition and management of coagulopathy in COVID-19" Jecko Thachil, et al., J Thromb Haemost. 2020;18:1023-1026. DOI: 10.1111/jth.14810.
Orini G, Brandazza A, Sarmientos P, Molinari A, Lansen J, Cauet G., "Efficient renaturation and fibrinolytic properties of prourokinase and a deletion mutant expressed in *Escherichia coli* as inclusion bodies," European Journal of Biochemistry (1991), 195, pp. 691-697.
Liu J N, Liu J X, Liu B, Sun Z, Zuo J L, Zhang J, et al., "A prourokinase mutant which induces highly effective clot lysis without interfering with hemostasis," Circulation Research (Apr. 19, 2002), 90, pp. 757-763.

* cited by examiner

*Primary Examiner* — Kade Ariani
(74) *Attorney, Agent, or Firm* — Ladas & Parry, LLP

(57) ABSTRACT

A method for prophylaxis and/or treatment of coagulopathy in a subject caused by a viral infection is provided. The method includes administering prourokinase or its variant; the viral infection is caused by a coronavirus.

8 Claims, 5 Drawing Sheets

USE OF PROUROKINASE AND ITS VARIANTS AGAINST COAGULOPATHY CAUSED BY VIRUSES

CROSS-REFERENCE TO RELATED APPLICATION

This application claims priority to Chinese application No. 202010726926.4, filed on Jul. 26, 2020, the disclosure of which is hereby incorporated by reference in its entirety.

TECHNICAL FIELD

The invention relates to the technical field of bio-pharmaceuticals, and in particular relates to use of prourokinase and its variants against coagulopathy caused by viruses.

BACKGROUND

Human prourokinase (unless otherwise indicated, the term "prourokinase" as used herein refers specifically to "human prourokinase" or prouk) is a single-chain urokinase-type plasminogen activator composed of 411 amino acids (see FIG. 1). Prourokinase structurally comprises three domains, namely an epidermal growth factor-like domain, a kringle domain, and a protease domain, among which the protease domain is responsible for activating plasminogen and generating its thrombolytic effect. A variant form of prourokinase is LMW-prouk (low-molecular-weight prourokinase), which comprises only a single protease domain among the three domains, that is, the structural region from position 135 to 411 in the amino acid sequence. M5 is another variant of prourokinase, obtained by mutating lysine 300 to a histidine in the amino acid sequence of prourokinase.

The 2019 novel coronavirus (COVID-19) infection is clinically manifested in several phenotypes, from asymptomatic to deep and rapid multiple organ dysfunction syndrome (MODS) and even death. The pathogenesis of MODS caused by COVID-19 is multi-factorial, and one important factor is coagulopathy, the clinical manifestations of which are a hypercoagulable state and thrombosis. Among COVID-19 patients, disseminated intravascular coagulation (DIC) is an important predictor of mortality: 71.4% of non-survivors and only 0.6% of survivors have DIC. On days 10 to 14 since diseased, non-survivors have significantly increased D-dimer and decreased fibrinogen, suggesting symptoms of blood clotting. More seriously, due to coagulation and thrombosis caused by the virus, COVID-19 patients often suffer from serious coagulopathy, such as ST-segment elevation myocardial infarction (STEMI), ischemic stroke (IS), pulmonary embolism (PE), deep veins thrombosis (DVT), and venous thromboembolism (VTE).

Although anticoagulant drugs such as low-molecular-weight heparin have been used for prevention of abnormal coagulation in COVID-19 patients (see FIG. 2), it was reported that severe COVID-19 patients receiving 30 to 40 mg of low-molecular-weight heparin (subcutaneous injection, once a day) still showed a very high incidence of DVT in lower limbs (85.4%) (see Reference 1). This suggests that in severe COVID-19 patients, anticoagulant drugs alone may not be enough to prevent thrombosis. Therefore, in clinical applications, thrombolytics with no risk of bleeding would be a solution to this fatal problem.

SUMMARY

Having made an analysis of all current thrombolytic drugs, the applicant has found that thrombolytics such as tPA and its derivatives, streptokinase, urokinase, and staphylokinase rapidly activate plasminogen after entering the bloodstream, no matter whether there is a thrombus in blood vessel or not, posing a risk of systemic bleeding. Here the applicant experimentally demonstrates that prourokinase and its variants are the sole drug candidates suitable to meet the above clinical requirements. Prourokinase has dual properties of a zymogen and an enzyme. Under physiological conditions, it is inert in plasma as a zymogen and will not activate plasminogen in the blood. However, when there is a thrombus formed in blood vessel, prourokinase can specifically activate the plasminogen bound to the thrombus, and then activated plasmin converts the prourokinase near the thrombus into urokinase. After the conversion into urokinase, the catalytic activity may increase by 250 to 500 times, which in turn massively activates all plasminogen bound on the thrombus and the free plasminogen around the thrombus, so that the thrombus is quickly dissolved. In this process, the action of protease inhibitors (α-antiplasmin, al macroglobulin, PAI-1, etc.) in the blood confines the effects of these urokinase and plasmin in the vicinity of a thrombus. Therefore, the thrombolytic effect induced by prourokinase is different from that of urokinase, streptokinase, or the like, and has thrombus specificity. As compared with tPA, prourokinase has the inertness of zymogen which prevents it from consuming the fibrinolytic enzyme inhibitors in the blood before coming into contact with an embolism or thrombus, thereby substantially preventing the side effects of systemic bleeding due to activation of systemic fibrinolysis.

The applicant has discovered in research that prourokinase and its variants have the following two characteristics:

1. When present below a certain concentration, prourokinase and its variants exist in an inert state in plasma and do not show the activity of activating plasminogen. This is illustrated in Experiment 1 below.

2. When a thrombus is formed or presented, prourokinase and its variants at any concentration can activate the plasminogen on the surface of the thrombus or around to exert their thrombolytic effect for clots lysis. This is illustrated in Experiment 2 below.

The applicant has discovered in research that the above two characteristics of prourokinase and its variants are both related to the protease domain. See the relevant data of LMW-prouk in Experiments 1 and 2 below. LMW-prouk contains only a single protease domain among the three domains of prourokinase, that is, the structural region from position 135 to 411 in the amino acid sequence. Therefore, any variants of prourokinase containing the protease domain of prourokinase can have the above characteristics and should fall within the applicable scope of the present invention.

The applicant has discovered in research that use of prophylactic doses of prourokinase or its variants in virus-infected patients can effectively prevent formation of thrombi and clots without increasing the risk of bleeding, thereby effectively preventing coagulopathy, such as disseminated intravascular coagulation, ST-segment elevation myocardial infarction, ischemic stroke, pulmonary embolism, deep veins thrombosis, and venous thromboembolism caused by the virus. When virus infection causes thrombosis in a patient, a thrombolytic therapy with therapeutic doses of prourokinase or its variants can effectively dissolve the thrombus and lower the risk of death and disability. The present invention fully demonstrates use of prourokinase and its variants in both prophylaxis and treatment of viral infections that cause coagulopathy, and the use can reduce the damage and possible sequelae caused by the virus to patients, and improve survival of the patients.

The present invention may be embodied through the following technical solutions.

Use of prourokinase and its variants in prophylaxis and/or treatment of coagulopathy caused by viruses, wherein:

For prophylaxis of coagulopathy caused by viruses, prourokinase is administered at the following dose (hereinafter "miu" means "million units") via the following administration route:

1) Intravenous drip: 1 to 5 miu/hr, continuous administration for 24 hours a day, or 6-hour to 7-hour administrations each followed by a 1-hour to 2-hour break, for consecutive 1 to 7 days;

or

2) Intravenous drip: 1 to 5 miu/hr, continuous administration for 24 hours a day, or 6-hour to 7-hour administrations each followed by a 1-hour to 2-hour break, for consecutive 1 to 7 days, combined with low-molecular-weight heparin (subcutaneous injection, once a day) or other anticoagulant drugs.

Preferably, for prophylaxis of coagulopathy caused by viruses, prourokinase is administered at the following dose via the following administration route:

1) Intravenous drip: 3 miu/hr, continuous administration for 24 hours a day, or 6.5-hour administrations each followed by a 1.5-hour break, for consecutive 1 to 7 days;

or

2) Intravenous drip: 3 miu/hr, continuous administration for 24 hours a day, or 6.5-hour administrations each followed by a 1.5-hour break, for consecutive 1 to 7 days, combined with low-molecular-weight heparin (subcutaneous injection, once a day) or other anticoagulant drugs.

For treatment of coagulopathy caused by viruses, prourokinase is administered at the following dose via the following administration route:

1) Intravenous drip: 5 to 8 miu/hr, until the thrombus disappears;

or

2) Intravenous drip: 5 to 8 miu/hr, plus TNK-tPA intravenous bolus once every 1 to 3 hours with 1 to 25 mg each time, until the thrombus disappears;

or

3) Intravenous drip: 5 to 8 miu/hr, plus TNK-tPA intravenous catheter administration at the site of thrombus, once every 1 to 3 hours with 1 to 25 mg each time, until the thrombus disappears.

For treatment of coagulopathy caused by viruses, prourokinase is preferably administered at the following dose via the following administration route:

1) Intravenous drip: 6 miu/hr, until the thrombus disappears;

or

2) Intravenous drip: 6 miu/hr, plus TNK-tPA intravenous bolus once every 1 to 3 hours with 5 mg each time, until the thrombus disappears;

or

3) Intravenous drip: 6 miu/hr, plus TNK-tPA intravenous catheter administration at the site of thrombus, once every 1 to 3 hours with 5 mg each time, until the thrombus disappears.

The "miu" used according to the present invention means "million international units"; and the "hr" according to the present invention means "hours".

Use of prourokinase and its variants in prophylaxis and/or treatment of coagulopathy caused by viruses, wherein:

1) For prophylaxis of coagulopathy caused by viruses, the dose of prourokinase or its variants is determined according to its inert concentration in plasma, usually not exceeding 70% of the inert concentration, while the administration route and the combination with other drugs are the same as those in the regime described above for the prophylactic use of prourokinase.

2) For treatment of coagulopathy caused by viruses, the dose of prourokinase or its variants required for a thrombolytic therapy is determined according to the effective thrombolytic dose, while the administration route and the combination with other drugs are the same as those in the regime described above for the treatment use of prourokinase.

The viruses include coronavirus.

The coronavirus includes but is not limited to the novel coronavirus (severe acute respiratory syndrome coronavirus 2 or SARS-CoV-2).

The coagulopathy described therein include, but are not limited to, disseminated intravascular coagulation, ST-segment elevation myocardial infarction, ischemic stroke, pulmonary embolism, and deep vein thrombosis caused by viruses.

Prourokinase or its variants used for prophylaxis or treatment are active ingredients prepared into pharmaceutical formulations.

The pharmaceutical formulation described herein includes injections.

The pharmaceutical formulation includes powder injections.

The powder injection may be a freeze-dried powder injection, and the raw and auxiliary materials of the freeze-dried powder injection may be prourokinase or its variants as active ingredients and mannitol.

The prourokinase according to the present invention is prouk for short, including prourokinase of natural, recombinant, and synthetic origins.

The variants of prourokinase according to the present invention include all variants of prourokinase that are consistent with the structural and activity characteristics of the protease domain of prourokinase.

The variants of prourokinase according to the present invention include, but are not limited to, the recombinant human prourokinase mutant obtained according to the preparation example of Chinese patent application CN00109829.2.

For a method for preparation of LMW-prouk according to the present invention, please refer to the following document:

Orini G, Brandazza A, Sarmientos P, Molinari A, Lansen J, Cauet G. Efficient renaturation and fibrinolytic properties of prourokinase and a deletion mutant expressed in *Escherichia coli* as inclusion bodies. European Journal of Biochemistry. 1991; 195:691-697.

For a method for preparation of M5 according to the present invention, please refer to the following document:

Liu J N, Liu J X, Liu B, Sun Z, Zuo J L, Zhang J, et al. A prourokinase mutant which induces highly effective clot lysis without interfering with hemostasis. Circulation Research 2002; 90: 757-763.

DESCRIPTION OF DRAWINGS

FIG. 3-1 is the experimental results of the stability (inertness) of prourokinase in human plasma.

FIG. 3-2 is the experimental results of the stability (inertness) of prourokinase variant M5 in human plasma.

FIG. 3-3 is the experimental results of stability (inertness) of prourokinase variant LMW-prouk in human plasma.

FIG. 4-1 shows the experimental results of the in vitro human plasma clot-dissolving effect of prourokinase.

FIG. 4-2 shows the experimental results of the in vitro human plasma clot-dissolving effect of prourokinase variant M5.

FIG. 4-3 shows the experimental results of the in vitro human plasma clot-dissolving effect of prourokinase variant LMW-prouk.

EXPERIMENTAL EXAMPLES

Figure 1:
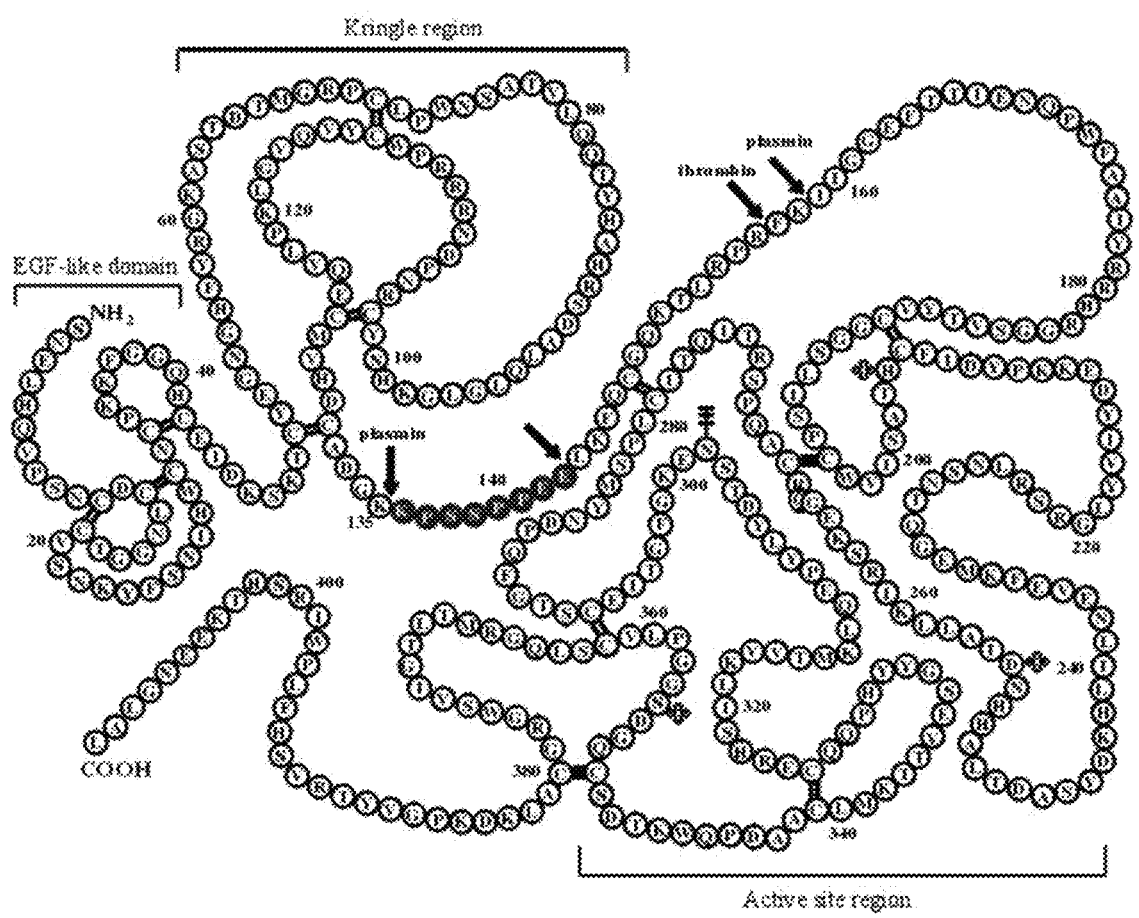
FIG. 1 is a schematic representation of the primary structure of human prourokinase.

The following specific experimental examples are used to illustrate the technical solutions of the present invention, but the scope of protection of the present invention is not limited thereto.

The contents of the experimental examples in this specification are only exemplary embodiments of the inventive concept. The scope of protection of the present invention should not be construed as limited to the specific embodiments given in the experimental examples, but also extends to the equivalent technical means that can be conceived by a person skilled in the art based on the inventive concept. Although the embodiments of the present invention are described below, the present invention is not limited to the specific embodiments and application fields, and the following specific embodiments are only illustrating and guiding rather than limiting. In light of this specification and without departing from the scope of protection of the claims of the present invention, a person ordinarily skilled in the art can make many other forms, which all fall within the scope of protection of the present invention.

All the quantitative tests in the following experimental examples are each repeated three times, and the data is given as the average value of the three repeated tests or as the average±standard deviation.

Experiment 1—the Study on the Stability (Inertness) of Prourokinase (Prouk) and its Variants in Human Plasma Method: Prouk (0.5-2 µg/mL) or M5 (6-12 µg/mL) or LMW-prouk (0.25-1 µg/mL) was added to 1.0 mL citrated plasma, and incubated at 37° C. for 7 days. A sample was taken every day, to which 0.2 mL aprotinin (10,000 kallikrein inhibitor units/mL) was added to stop the reaction, and then the residual fibrinogen in the plasma was measured and compared with a baseline.

Results: After incubation in citrated plasma at 37° C. for 7 days, prouk remained inert at a concentration of 1 µg/mL, but was capable of inducing degradation of fibrinogen when its concentration reached 2 µg/mL (see FIG. 3-1); M5 was inert until a concentration limit of 8 µg/mL, and caused degradation of fibrinogen when it reached 10 µg/mL (see FIG. 3-2); and LMW-prouk was inert until a limit of 0.5 µg/mL, and caused degradation of fibrinogen when it reached 1 µg/mL (see FIG. 3-3).

Experiment 2—the Study on In Vitro Clots Lysis in Human Plasma by Prouk and its Variants Method: $^{125}$I-labeled fibrinogen clots were prepared with 0.2 mL plasma, and put in 4 mL plasma, to which prouk (0.5-1.5 µg/mL) or M5 (0.5-5 µg/mL) or LMW-prouk (0.25-1 µg)/mL) was added, and co-incubated at 37° C. to examine the lysis of blood clots. The experiment ended when the blood clots in the highest-concentration group were completely dissolved, and the lysis at other concentrations was also examined.

Figure 2:
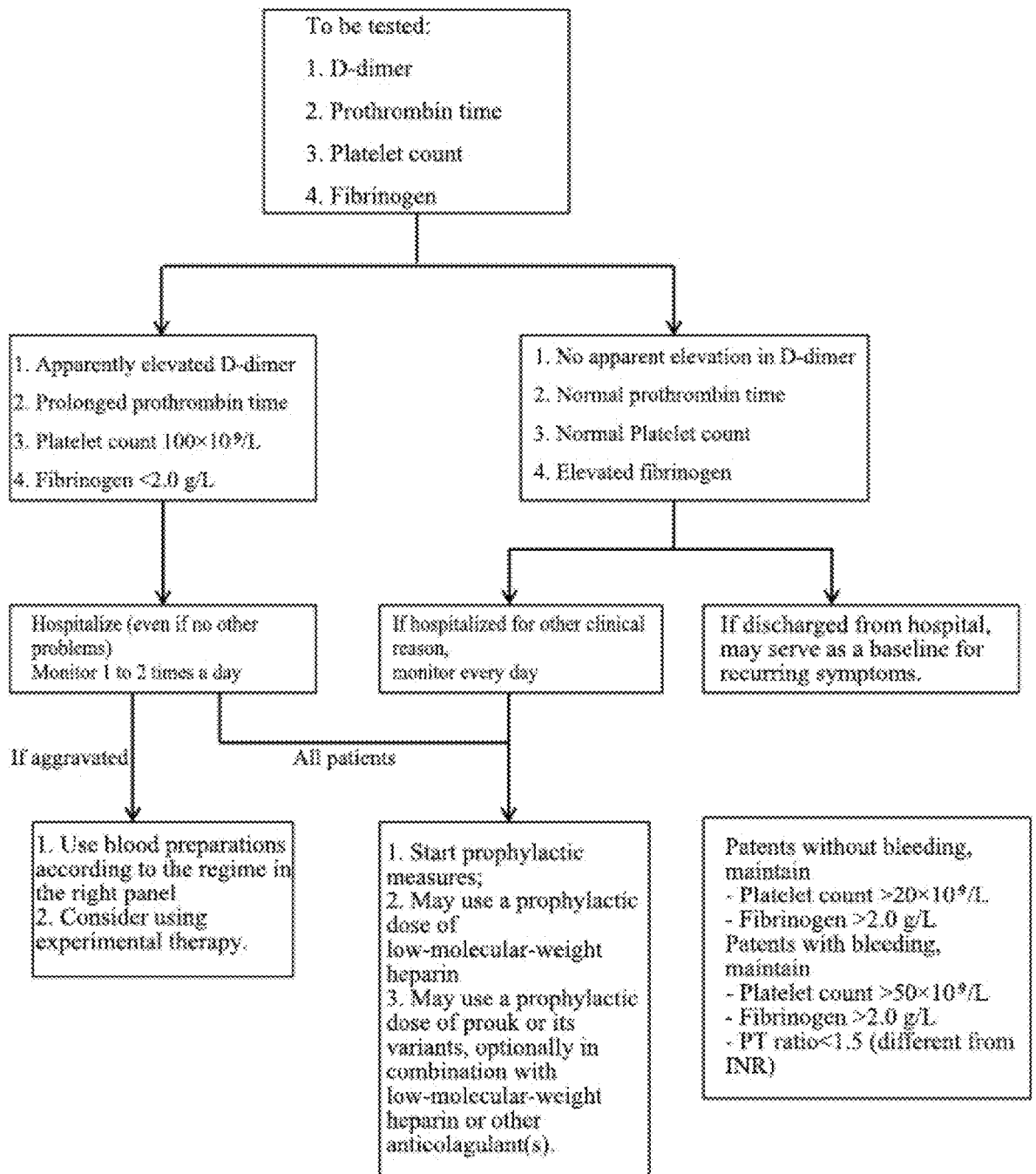
FIG. 2 shows the process of diagnosis and anticoagulation treatment of Covid-19 patients with hypercoagulability.
Figures 1, 3:
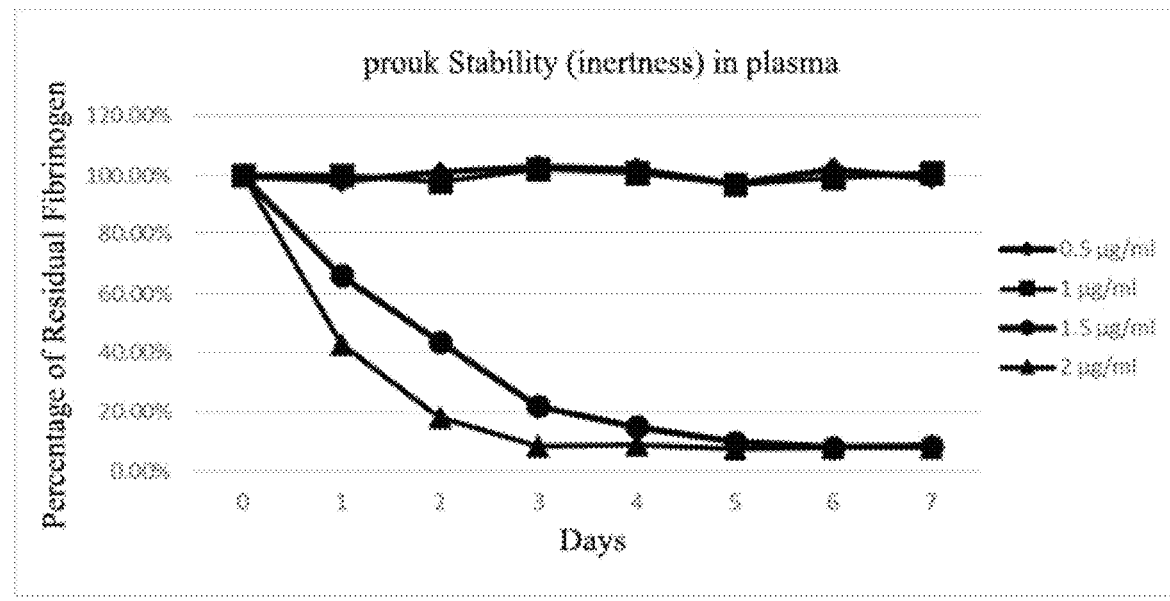
Figures 2, 3:
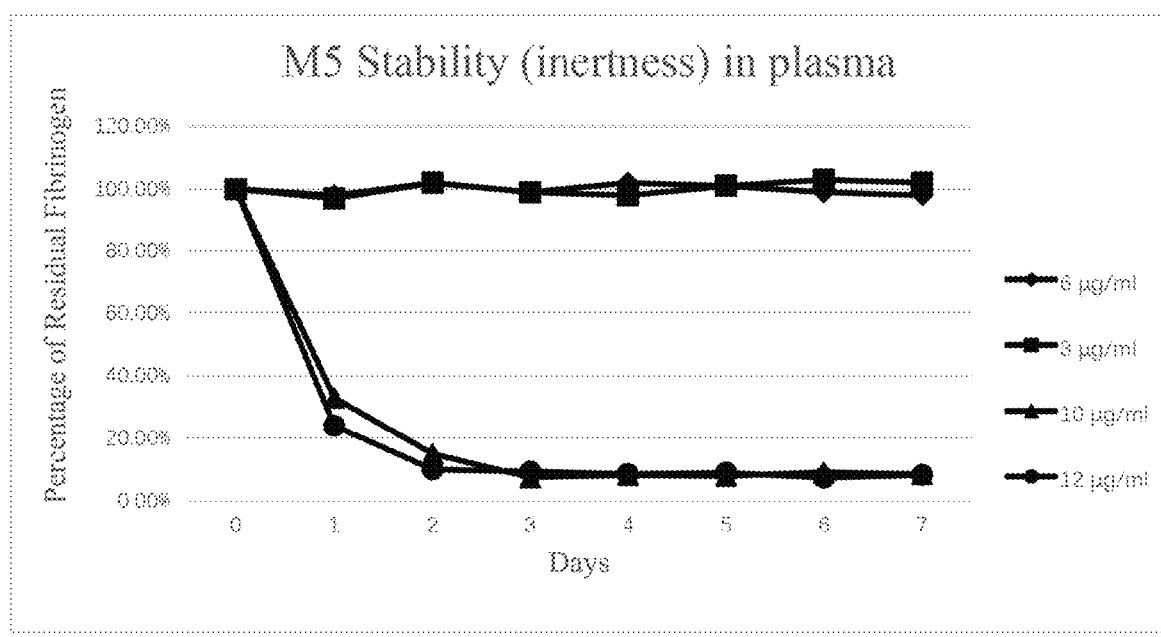
Figure 3:
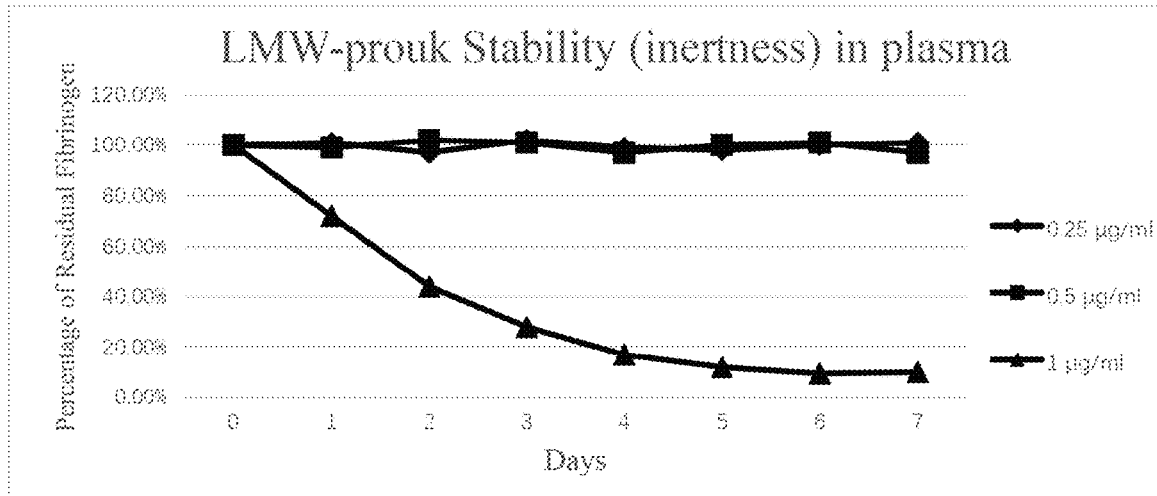
Figures 1, 4:
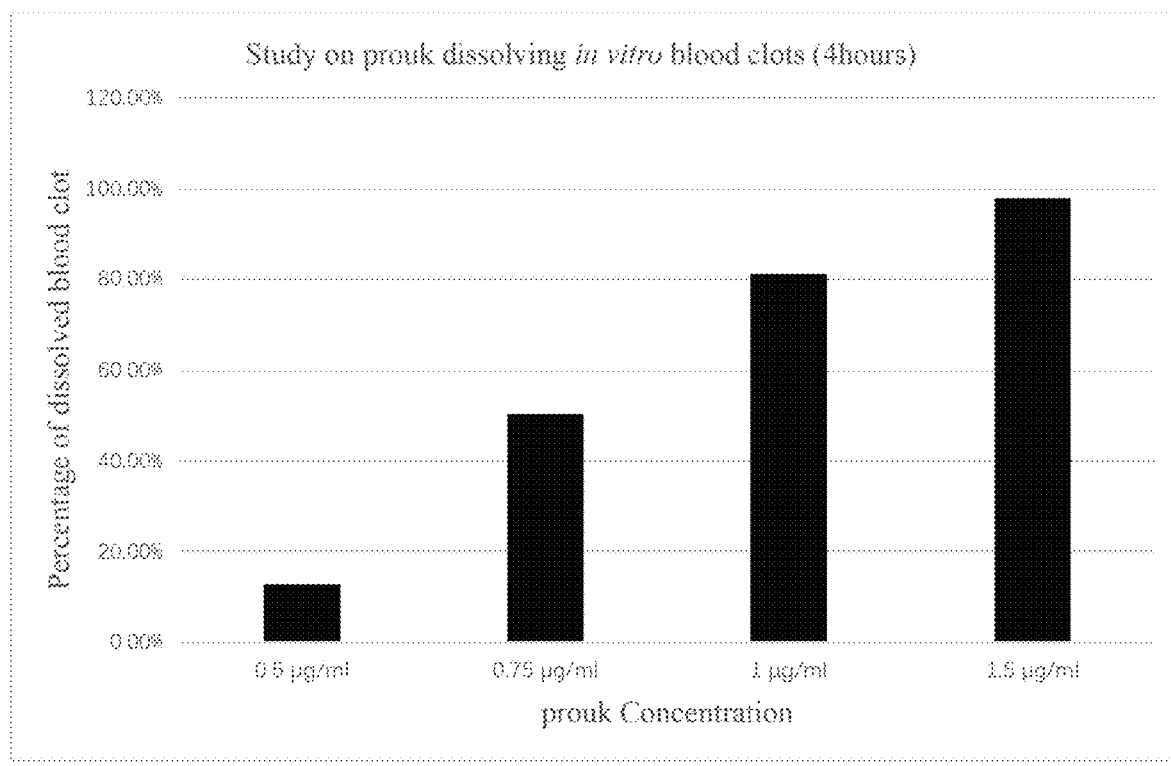
Figures 2, 4:
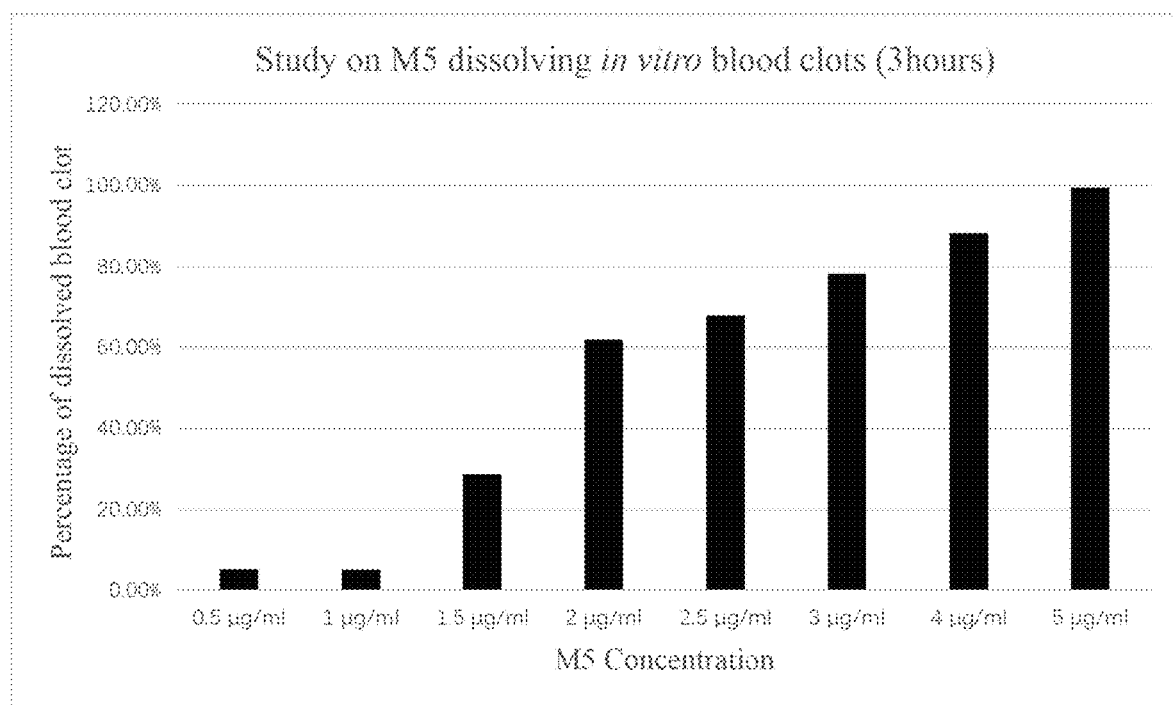
Figures 3, 4:
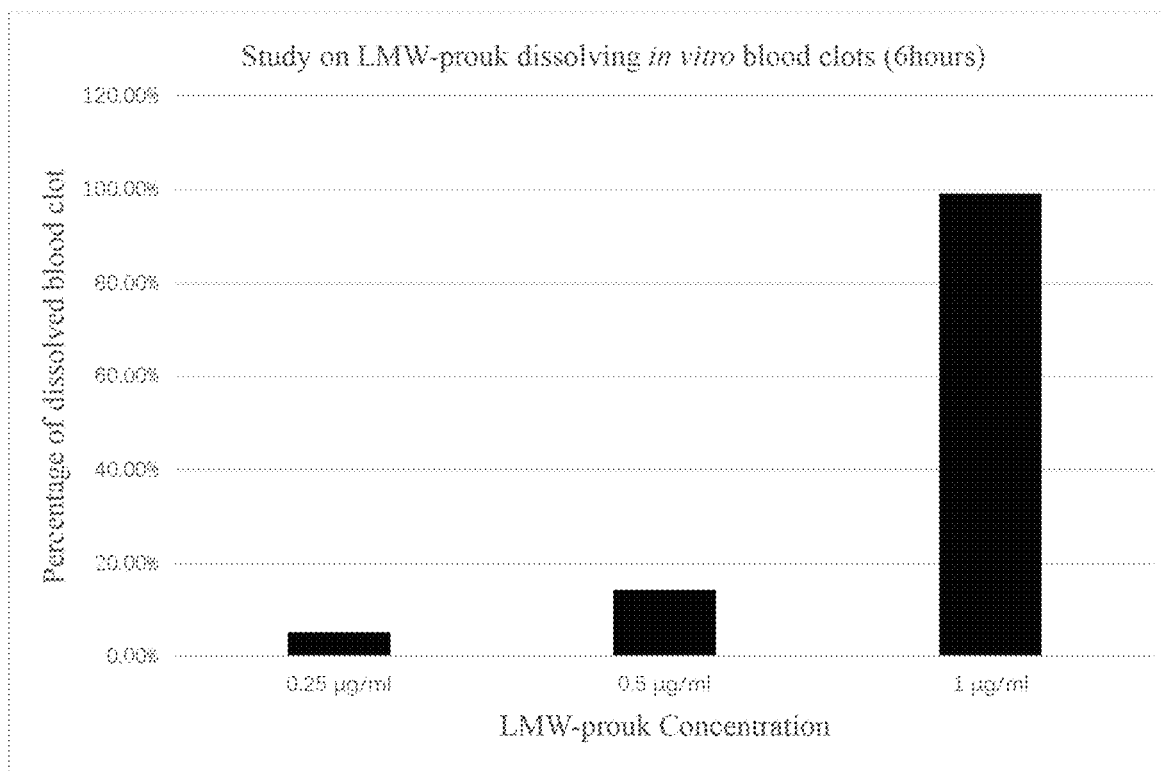

Result: prouk at 1.5 µg/mL completely dissolved the blood clots in 4 hours, and lysis at the other concentrations is shown in FIG. 4-1; M5 at 5 µg/mL completely dissolved the blood clots in 3 hours, and lysis at the other concentrations is shown in FIG. 4-2; LMW-prouk at 1 µg/mL completely dissolved the blood clots in 6 hours, and lysis at the other concentrations is shown in FIG. 4-3. The results of LMW-prouk proved that the thrombolytic ability of prourokinase and its variants came from the protease domain.

Experiment 3—the Study on the Safety of Prouk Intravenously Administrated in Monkeys Method: To study the safety of prouk, a safety test was carried out on cynomolgus monkeys. They were administered by intravenous drip at doses of 0.57 mg/(kg·hr), 0.86 mg/(kg·hr), and 1.15 mg/(kg·hr) for consecutive 10 days, wherein each 6.5-hour administration was followed by a 1.5-hour break. A sample was taken every day to test the blood fibrinogen content, and whether an adverse effect such as bleeding occurred was observed.

Results: The blood fibrinogen content of monkeys in all test groups remained stable during the continuous administration period, and no adverse effect such as bleeding was observed.

Experiment 4—the Pharmacokinetics of Prouk and its Variants

1. The Pharmacokinetic Study on Prouk

Method: Administrations at 0.29 mg/(kg·hr) or 0.57 mg/(kg·hr) to human bodies were conducted by continuous intravenous drip, and changes in the blood drug concentration were examined.

Results: For the study group administered intravenously at a dose of 0.29 mg/(kg·hr), the maximum blood concentration was reached at 20-30 minutes, and the average maximum blood concentration was 0.68 µg/mL; for the study group administered intravenously at a dose of 0.57 mg/(kg·hr), the maximum blood concentration was reached at 20-30 minutes, and the average maximum blood concentration was 1.43 µg/mL.

2. The Pharmacokinetic Study on LMW-Prouk

The pharmacokinetic study on LMW-prouk was conducted according to the experimental method for prouk, and the experimental results were basically the same as those for prouk, without a significant difference.

Experiment 5—Clinical Dosing Regime

1. Eligible people were determined according to the process shown in FIG. 2.

2. Dosage and administration route of prourokinase

For prophylaxis (no thrombosis in the patient):

1) Intravenous drip: 3 miu/hr (1-5 miu/hr), 24 hrs, or by 6.5-hr (6 to 7 hr) administrations each followed by a 1.5-hr (1 to 2 hr) break, for 1-7 days.

or

2) Intravenous drip: 3 miu/hr (1-5 miu/hr), 24 hrs, or by 6.5-hr (6 to 7 hr) administrations each followed by a 1.5-hr (1 to 2 hr) break, for 1-7 days, in combination with administration of low-molecular-weight heparin or other anticoagulant drug(s).

For treatment (with thrombosis):

1) Intravenous drip: 6 miu/hr (5 to 8 miu/hr) until the thrombus disappears.

or

2) Intravenous drip: 6 miu/hr (5 to 8 miu/hr), plus TNK-tPA intravenous bolus, once every 1-3 hours, 5 mg (1 to 25 mg) each time, until the thrombus disappears.

or

3) Intravenous drip: 6 miu/hr (5 to 8 miu/hr), plus TNK-tPA intravenous catheter administration at the site of thrombus, once every 1-3 hours, 5 mg (1 to 25 mg) each time, until the thrombus disappears.

3. Dosage and administration route of variants of prourokinase

1) For prophylaxis of coagulopathy caused by viruses, the dose of variants of prourokinase was determined according to its inert concentration in plasma, usually not exceeding 70% of the inert concentration, while the administration route and combination with other drugs were the same as those for the prophylactic use of prourokinase.

2) For treatment of coagulopathy caused by viruses, the dose of variants of prourokinase required for a thrombolytic therapy was determined according to its effective thrombolytic dose, while the administration route and combination with other drugs were the same as those for the treatment use of prourokinase.

Conclusion: (1) after prophylactic administration to patients infected with the novel coronavirus, the incidence of coagulopathy in the patients was significantly reduced, without adverse effects such as bleeding in patients observed, which fully demonstrates that prourokinase and its variants according to the present invention can effectively prevent coagulopathy caused by the virus, without causing significant adverse effects and with good safety; (2) after therapeutic administration to patients infected with the novel coronavirus, the damage caused by thrombi to the patients was effectively controlled, and the potential risk of death was reduced. In terms of both prophylaxis and treatment, it is fully demonstrated that prourokinase and its variants can be used against viral infections that cause coagulopathy, can reduce the damage and possible sequelae caused by viruses to patients, and can improve the survival of patients.

The examples of the present invention include but are not limited to those described above.

REFERENCES

1. Ren, Yan, Deng, Zhang, et al., (2020); Extremely High Incidence of Lower Extremity Deep Venous Thrombosis in 48 Patients with Severe COVID-19 in Wuhan, 10.1161/CIRCULATIONAHA.120.047407.

2. ISTH interim guidance on recognition and management of coagulopathy in COVID-19. doi: 10.1111/JTH.14810.

The invention claimed is:

1. A method for prophylaxis and/or treatment of coagulopathy caused by a coronavirus infection in a subject, the method comprising administering to the subject in need prourokinase or a variant thereof.

2. The method according to claim 1, wherein for the prophylaxis of coagulopathy, the prourokinase is administered by an administration route and dosage selected from the group consisting of:

Intravenous drip: 1 to 5 miu/hr, continuous administration for 24 hours a day, or 6-hour to 7-hour administrations each followed by a 1-hour to 2-hour break, for consecutive 1 to 7 days;

or

Intravenous drip: 1 to 5 miu/hr, continuous administration for 24 hours a day, or 6-hour to 7-hour administrations each followed by a 1-hour to 2-hour break, for consecutive 1 to 7 days, combined with one or more anticoagulant drugs.

3. The method according to claim 1, wherein for the treatment of coagulopathy, the prourokinase is administered by an administration route and dosage selected from the group consisting of:

Intravenous drip: 5 to 8 miu/hr, until thrombus disappears;

or

Intravenous drip: 5 to 8 miu/hr, plus TNK-tissue plasminogen activator (TNK-tPA intravenous bolus once every 1 to 3 hours with 1 to 25 mg each time, until the thrombus disappears;

or

Intravenous drip: 5 to 8 miu/hr, plus TNK-tPA intravenous catheter administration at the site of thrombus, once every 1 to 3 hours with 1 to 25 mg each time, until the thrombus disappears.

4. The method according to claim 1, wherein the prourokinase or the variant thereof is in form of a pharmaceutical formulation.

5. The method according to claim 1, wherein the coagulopathy caused by the coronavirus infection is selected from the group consisting of disseminated intravascular coagulation, ST-segment elevation myocardial infarction (STEMI), ischemic stroke (IS), pulmonary embolism (PE), deep vein thrombosis (DVT) and venous thromboembolism (VTE).

6. The method according to claim 1, wherein the coronavirus is coronavirus SARS-CoV-2.

7. The method according to claim 4, wherein the pharmaceutical formulation further comprising an injectable formulation.

8. The method according to claim 7, wherein the pharmaceutical formulation further comprising a powder injection in form of a powder.

* * * * *